United States Patent [19]

Maldonado et al.

[11] Patent Number: 4,976,879

[45] Date of Patent: Dec. 11, 1990

[54] SULFOAROYL END-CAPPED ESTER OLIGOMERS SUITABLE AS SOIL-RELEASE AGENTS IN DETERGENT COMPOSITIONS AND FABRIC-CONDITIONER ARTICLES

[75] Inventors: Rene Maldonado, Holland, Pa.; Toan Trinh, Mainville; Eugene P. Gosselink, Cincinnati, all of Ohio

[73] Assignee: The Procter & Gamble Company, Cincinnati, Ohio

[21] Appl. No.: 399,727

[22] Filed: Aug. 28, 1989

Related U.S. Application Data

[62] Division of Ser. No. 105,421, Oct. 5, 1987.

[51] Int. Cl.$^5$ .................... C11D 3/34; C07C 309/28; D06M 13/256

[52] U.S. Cl. .................................... 252/8.7; 252/89.1; 252/121; 252/174.23; 8/137; 560/14

[58] Field of Search ....................... 252/8.7, 89.1, 121, 252/174.23; 8/137; 560/14

[56] References Cited

U.S. PATENT DOCUMENTS

| | | | |
|---|---|---|---|
| 3,416,952 | 12/1968 | McIntyre et al. | 117/118 |
| 3,546,008 | 12/1970 | Shields et al. | 117/138.8 |
| 3,563,942 | 2/1971 | Heikerger | 260/29.2 |
| 3,639,352 | 2/1972 | Katsuura et al. | 528/293 |
| 3,712,873 | 1/1973 | Zenk | 260/29.2 |
| 3,734,874 | 5/1973 | Kibler et al. | 260/29.2 |
| 3,821,169 | 6/1974 | Duddey | 528/293 |
| 3,853,820 | 12/1974 | Vachon | 260/75 |
| 4,116,885 | 9/1978 | Derstadt et al. | 252/532 |
| 4,132,680 | 1/1979 | Nicol | 252/547 |
| 4,145,518 | 3/1979 | Morie et al. | 528/272 |
| 4,156,073 | 5/1979 | Login | 528/295 |
| 4,161,577 | 7/1979 | Price et al. | 528/295 |
| 4,215,026 | 7/1980 | Login . | |
| 4,238,531 | 12/1980 | Rudy et al. | 252/8.6 |
| 4,304,900 | 12/1981 | O'Neill | 528/290 |
| 4,304,901 | 12/1981 | O'Neill et al. | 528/290 |
| 4,427,557 | 1/1984 | Stockburger | 252/8.7 |
| 4,525,524 | 6/1985 | Tung et al. | 524/601 |
| 4,554,328 | 11/1985 | Sinker et al. | 525/437 |
| 4,702,857 | 10/1987 | Gosselink | 252/8.6 |
| 4,721,580 | 1/1988 | Gosselink | 252/90 |
| 4,738,787 | 4/1988 | O'Lenick et al. . | |
| 4,759,876 | 7/1988 | Crossin et al. | 252/551 |

FOREIGN PATENT DOCUMENTS

| | | |
|---|---|---|
| 1100262 | 5/1981 | Canada . |
| 185427 | 6/1986 | European Pat. Off. . |
| 194127 | 9/1986 | European Pat. Off. . |
| 199403 | 10/1986 | European Pat. Off. . |
| 56-98230 | 8/1981 | Japan . |
| 57-25326 | 2/1982 | Japan . |
| 59-30967 | 2/1984 | Japan . |
| 60-250028 | 10/1985 | Japan . |
| 61-275422 | 12/1986 | Japan . |
| 1161668 | 8/1969 | United Kingdom . |
| 2172608 | 9/1987 | United Kingdom . |

OTHER PUBLICATIONS

Handbook of Fiber Science and Technology, Marcel Dekker, New York, N.Y., 1984, vol. II, Part B, Chapter 3, entitled "Soil Release Finishes", Polyesters and Their Applications, Bjorksten et al., Reinhold, 1956, pp. 156–173, 284 & 285, 322 & 323, 328 and 329.

Ponnusamy et al., Makromol. Chem. 184, 1279–1284, 1983, Zimmerman et al., Faserforsch. Textiltech., 18 (11), 536—7 as the Abstract, CA 68(2): 3741(g).

*Primary Examiner*—Paul Lieberman

*Assistant Examiner*—Alexander G. Hyka

*Attorney, Agent, or Firm*—Lars S. Johnson; Jerry J. Yetter; Richard C. Witte

[57] ABSTRACT

Anionic, especially sulfoaroyl, $NaO_3S(C_6H_4)$ C(O)— preferred, end-capped esters useful as soil release agents in detergent compositions and fabric-conditioner articles. The terephthalate esters contain unsymmetrically substituted oxy-1,2-alkyleneoxy units (oxy-1,2-propyleneoxy units preferred).

3 Claims, No Drawings

SULFOAROYL END-CAPPED ESTER OLIGOMERS SUITABLE AS SOIL-RELEASE AGENTS IN DETERGENT COMPOSITIONS AND FABRIC-CONDITIONER ARTICLES

This is a division of application Ser. No. 105,421, filed on Oct. 5, 1987.

TECHNICAL FIELD

The present invention relates to novel ester compositions useful as soil-releasing ingredients in laundry products such as granular detergents and dryer-added fabric conditioner sheets.

BACKGROUND OF THE INVENTION

A substantial proportion of synthetic fabrics now in use are copolymers of ethylene glycol and terephthalic acid, sold under trade names which include DACRON, FORTREL, KODEL and BLUE C POLYESTER. The removal of oily soil and oily stains from the surface of such fabrics is well recognized to be technically difficult to achieve using laundry compositions of the type most generally accessible to consumers.

Substances which have been suggested for use in consumer products as soil release agents include polymers which contain ethylene terephthalate segments randomly interspersed with polyethylene glycol segments. See, for example, U.S. Pat. No. 3,962,152, Nicol et al, issued June 8, 1976. A soil release polyester of this type, commercially known as MILEASE T, is further disclosed in U.S. Pat. No. 4,116,885, Derstadt et al, issued Sept. 7, 1978. Other commercial variants are sold as PERMALOSE, ZELCON and ALKARIL products (see, for example, Canadian Patent No. 1,100,262, Becker et al, issued May 5, 1981; U.S. Pat. No. 4,238,531, Rudy et al, issued Dec. 9, 1980; and British Patent Application No. 2,172,608, Crossin, published Sept. 24, 1986). Commercial suppliers of soil release polyesters include ICI, duPont and Alkaril (formerly Quaker Chemical Co.).

Soil release compositions used in industrial textile treatment applications are well-known. Application of such compositions is under controlled conditions and is free from the formulation constraints encountered in the detergent arts. Padding and heat curing, in the absence of high levels of detergent chemicals, are illustrative of the processes used. Polyesters have successfully been used for industrial soil release treatments of polyester surfaces, but recent trends are toward rather expensive fluorochemical treatments.

The development of economical, product-stable and formulation-compatible soil release agents for consumer product compositions is not straightforward. In contrast with the simple and controlled environments in which industrial textile treatment agents are generally used, soil release agents in consumer laundry products will usually be exposed to various detersive ingredients, such as anionic surfactants, alkaline builders and the like. Such chemicals may reduce the effectiveness of soil release agents, for example, by preventing their deposition on fabrics. The soil release agents may, reciprocally, reduce the laundry benefits of detersive ingredients, for example, by interfering with the action of surfactants, optical brighteners, antistatic agents or softeners, all of which are commonly present in modern detergent compositions. In a "thru-the-wash" mode, it is especially important that no formulation ingredient, including the soil release agent, should promote the redeposition of suspended soils in the laundry liquor; this would dull the appearance of the laundered fabrics.

Arguably, the most difficult of consumer laundry products, for the purpose of incorporating soil release agents, are granular detergent compositions. Compatibility requirements of soil release agents, especially with the alkaline, anionic detergent environments commonly present in such detergent compositions, provide a substantial technical challenge.

The end-capped esters of the present invention have been developed to meet these needs.

It is an object of the present invention to provide novel compositions which can be used as effective and product compatible soil release agents in consumer products having widely varying formulas, such as granular detergent compositions and fabric conditioner sheets.

It is a further object of the invention to provide novel ester oligomers and low molecular weight polyesters.

These and other objects are secured herein, as will be seen from the following disclosure.

BACKGROUND ART

Chemistry relevant to preparing the compositions of this invention includes aspects of what is colloquially known as "polyester chemistry" but, as opposed to high polymers such as fibrous or resinous polyesters with which polyester chemistry is principally concerned, novel linear, end-capped, low molecular weight, oligomeric esters or polymeric esters are provided herein.

A. Soil Release Finishes

Handbook of Fiber Science and Technology, Marcel Dekker, New York, N.Y., 1984, Volume II, Part B, Chapter 3, entitled "Soil Release Finishes", is a recent review of soil release agents. Almost all of the soil release agents reviewed appear to find application principally outside the laundry detergent arts. The polyesters are generally nonionic, and have relatively high molecular weights.

B. Polyester Chemistry

Polyesters and Their Applications, Bjorksten et al, Reinhold, 1956, reviews the older and well-established art of polyester synthesis, with particular emphasis on high molecular weight, e.g., fiber-forming polyesters, and polyesters usable for making shaped articles.

C. Polyester Backbones

Ponnusamy et al, Makromol. Chem. 184, 1279–1284 (1983), discloses a recent synthesis and characterization of copolyesters of ethylene glycol, 1,2-propylene glycol, or mixtures thereof, with dimethyl terephthalate. Molecular weights of the products range from 4,000–6,000. Chemically similar materials, having higher molecular weights, are disclosed in U.S. Pat. No. 4,145,518, Morie et al, issued Mar. 20, 1979.

D. Capping Reagents and Capped Polyesters

U.S. Pat. No. 4,525,524, Tung et al, issued June 25, 1985, discloses aryl carboxylate end-capped poly(glycol terephthalate) esters. These polyesters are said to have increased affinity for water-based systems. The arylcarboxylates used to form the preferred polyesters incorporate $NaO_3S$- groups.

E. End-capped Branched Polyesters

U.S. Pat. No. 4,554,328, Sinker et al, issued Nov. 19, 1985, discloses a modified polymer suitable for use in making hollow containers by conventional extrusion blow molding. The polymer is a terephthalate-based polyester of high molecular weight. The polyester is branched rather than linear, due to the incorporation of pentaerythritol, $C(C_2OH)_4$ as a branching agent, and is end-capped in preferred embodiments by means of the use of four moles of meta- sulfobenzoyl groups per mole of pentaerythritol.

F. Polyesters containing sulfonated groups not specifically situated at the polymer chain ends The polyester art making reference to incorporation of sulfonated aromatic groups in polyester backbones is very extensive; much of this art appears to relate to high-molecular weight, fiber-forming polyesters or polyesters used to make shaped articles. See, for example, the older art referenced above, or U.S. Pat. No. 3,416,952, McIntyre et al, issued Dec. 17, 1968. More recently, water-dissipatable or solvent-soluble polyesters containing sulfoaromatic groups have been disclosed. See, for example, U.S. Pat. Nos. 4,304,900 and 4,304,901, O'Neill, issued Dec. 8, 1981, and U.S. Pat. No. 3,563,942, Heiberger, issued Feb. 16, 1971. These patents disclose the utility as adhesives, coatings, films, textile sizes and the like of polyester compositions resembling those of the art but having particular sulfonated groups.

U.S. Pat. No. 4,427,557, Stockburger, issued Jan. 24, 1984, discloses copolyesters having relatively low (2,000 to 5,000) molecular weights, formed by the reaction of ethylene glycol, a PEG having an average molecular weight of 200 to 1,000, an aromatic dicarboxylic acid (e.g., dimethyl terephthalate), and a sulfonated aromatic dicarboxylic acid (e.g., dimethyl 5-sulfoisophthalate).

In connection with the incorporation of sulfonated aromatic dicarboxylates into polyesters, see also U.S. Pat. Nos. 3,853,820, Vachon, issued Dec. 10, 1984; 3,734,874, Kibler et al, issued May 22, 1973; and 3,546,008, Shields et al, issued Dec. 8, 1970.

G. Use of sulfobenzoyl derivatives as catalysts, modifiers and analytical reagents in polyester chemistry.

Zimmerman et al, Faserforsch. Textiltech., 18 (11), 536–7, 1967, report that o-sulfobenzoic anhydride can be used in a procedure for determining the hydroxyl end-groups in poly(ethylene terephthalate). Japanese Patent Documents Nos. 57/25326, Japan Ester Co., published Feb. 10, 1982 and 56/98230, Japan Ester Co., published Aug. 7, 1981 report the use of $3\text{–}4\times10^{-4}$ molar o- and m- sulfobenzoic acids as catalysts in the synthesis of high molecular weight poly(ethylene terephthalate). Japanese Patent Document No. 61/275422, Teijin Ltd., published Dec. 5, 1986, discloses the use of 2 mole % (based on terephthalate) of sodium 2-hydroxyethyl m-sulfobenzoate as a modifier for use during synthesis of polyester fibers.

H. Prepolymers and sulfobenzoyl catalysts in polyester synthesis

Japanese Patent Document No. 60/250028, Nippon Ester, published Dec. 10, 1985, discloses prepolymerization of bis(hydroxyethyl)terephthalate to form a prepolymer having low intrinsic viscosity, which is further polymerized in the presence of sulfonic acid derivatives such as benzenesulfonic acid and o-sulfobenzoic anhydride; propylene glycol, 1,4-cyclohexanedimethanol or pentaerythritol can optionally be present.

I. Ethylene terephthalate/PEG terephthalate soil release polyesters used in laundry detergent and related consumer-usable compositions U.S. Pat. No. 4,116,885, Derstadt et al, issued Sept. 26, 1978, discloses laundry detergent compositions containing from 0.15 to 25% (most preferably 0.5 to 10%) of an ethylene terephthalate/PEG terephthalate soil release polyester, such as MILEASE T.

U.S. Pat. No. 4,132,680, Nicol, issued Jan. 2, 1979, also discloses laundry detergent compositions having soil release properties which comprise a soil release polyester having a molecular weight of 10,000 to 50,000, e.g., MILEASE T.

Polyesters have also been disclosed for use in rinse-added consumer laundry products, in dryer-added products, and in certain built liquid detergents. See Canadian Patent No. 1,100,262, Becker et al, issued July 8, 1975; U.S. Pat. No. 3,712,873, Zenk, issued Jan. 23, 1973; U.S. Pat. No. 4,238,531, Rudy et al, issued Dec. 9, 1980; and British Patent Application No. 2,172,608, Crossin, published Sept. 24, 1986.

SUMMARY OF THE INVENTION

The present invention encompasses oligomeric or low molecular weight polymeric, substantially linear, sulfoaroyl end-capped esters, said esters comprising unsymmetrically substituted oxy-1,2-alkyleneoxy units, and terephthaloyl units, in a mole ratio of said unsymmetrically substituted oxy-1,2-alkyleneoxy units to said terephthaloyl units ranging from about 2:1 to about 1:24. (Mixtures of such esters with reaction by-products and the like retain their utility as fabric soil release agents when they contain at least 10% by weight of said linear, end-capped esters.) The esters herein are of relatively low molecular weight (i.e., outside the range of fiber-forming polyesters) typically ranging from about 500 to about 20,000.

The essential end-capping units herein are anionic hydrophiles, connected to the esters by means of aroyl groups. Preferably, the anion source is a sulfonated group, i.e., the preferred end-capping units are sulfoaroyl units, especially these of the formula $(MO_3S)(C_6H_4)C(O)$—, wherein M is a salt-forming cation such as Na or tetraalkylammonium.

The essential "unsymmetrically substituted oxy-1,2-alkyleneoxy" units of the esters herein are units selected from the group consisting of (a) —$OCH(R^a)CH(R^b)O$— units, wherein $R^a$ and $R^b$ are selected so that in each of said units, one of said groups is H and the other is a non-hydrogen R group, and (b) mixtures of the foregoing units wherein the non-hydrogen R groups are different. Mixtures of the unsymmetrical units (a) or (b) with —$OCH_2CH_2O$— units are also acceptable, provided that the units taken together have, overall, a sufficiently unsymmetrical character. A convenient measure of the unsymmetrical character required is given by the mole ratio of units (a) or (b) to —$OCH_2CH_2O$— units, which must lie in the range from about 1:10 to about 1:0. In the above, R is always a nonhydrogen, noncharged group, has low molecular weight (typically below about 500), is chemically unreactive (especially in that it is a nonesterifiable group), and is comprised of C and H, or of C,H and O. In the above-defined mixtures of units (a) or (b) with $-OCH_2CH_2O-$ units, specifically excluded are poly(oxyethylene)oxy units, i.e., $-(OCH_2CH_2)_nO-$ wherein n is a number greater than or equal to 2; (such poly(oxyethylene)oxy units form a separate category of units the use of which is optional, as further defined hereinafter). The preferred R groups are selected from the group consisting of lower n-alkyl groups, such as methyl, ethyl, propyl and butyl. Thus, the preferred oxy-1,2-alkyleneoxy units are oxy-1,2-propyleneoxy, oxy-1,2-butyleneoxy, oxy-1,2-pentyleneoxy and oxy-1,2-hexyleneoxy units. Especially preferred by way of oxy-1,2-alkyleneoxy units are oxy-1,2-propyleneoxy units (a), and mixtures thereof with oxyethyleneoxy units in the above-defined mole ratios.

Certain noncharged, hydrophobic aryldicarbonyl units are also essential herein. Preferably, these are exclusively terephthaloyl units. Other noncharged, hydrophobic aryldicarbonyl units, such as isophthaloyl or the like, can also be present if desired, provided that the soil release properties of o the esters (especially polyester substantivity) are not significantly diminished.

It is also possible optionally to incorporate additional hydrophilic units into the esters. These may be nonionic hydrophilic units, such as poly(oxyethylene)oxy units; in another example, anionic hydrophilic units capable of forming two ester bonds may be used. Suitable anionic hydrophilic units of this specific type are well illustrated by sulfonated carbonyl units, such as sulfosuccinyl, i.e.

$$NaO_3SCH[C(O)]CH_2C(O)-;$$

or more preferably, sulfoisophthaloyl, i.e., $-(O)C(C_6H_3)(SO_3M)C(O)-$ wherein M is a salt-forming cation.

Generally, herein, if it is desired to modify the units of the esters, use of additional hydrophilic units is preferable to use of additional noncharged, hydrophobic units.

Thus, preferred esters herein comprise, per mole of said ester, (i) from about to about 2 moles of sulfobenzoyl end-capping units of the formula $(MO_3S)(C_6H_4)C(O)-$ wherein M is a salt-forming cation;

(ii) from about 2 to about 50 moles of oxy-1,2-propyleneoxy units or mixtures thereof with oxyethyleneoxy units; and (iii) from about 1 to about 40 moles of terephthaloyl units.

The "backbone" of the esters herein may further optionally comprise, per mole of said ester, (iv) from 0 to about 30 moles of 5-sulfoisophthaloyl units of the formula $-(O)C(C_6H_3)(SO_3M)C(O)-$ wherein M is a salt-forming cation; or (v) from 0 to about 25 moles of poly(oxyethylene)oxy units of the formula $-(OCH_2CH_2)_nO-$ wherein the average degree of ethoxylation n ranges from 2 to about 100; or (vi) from 0 to about 30 moles of a mixture of said units (iv) and (v) at a (iv):(v) mole ratio of from about 29:1 to about 1:29.

The end-capping sulfoaroyl units used in these esters are preferably sulfobenzoyl as in (i), and most preferably not more than about 0.15 mole fraction of said sulfobenzoyl end-capping units are in para- form. Most highly preferred are esters wherein said sulfobenzoyl end-capping units are essentially in ortho- or meta-form.

Preferred end-capped esters herein are essentially in the doubly end-capped form, comprising about 2 moles of said sulfobenzoyl end-capping units per mole of said ester.

The ester "backbone" of the present compositions, by definition, comprises all the units other than the end-capping units; all the units incorporated into the esters being interconnected by means of ester bonds. Thus, in one simple preferred embodiment, the ester "backbones" comprise only terephthaloyl units and oxy-1,2-propyleneoxy units. In other preferred embodiments incorporating oxyethyleneoxy units, the ester "backbone" comprises terephthaloyl units, oxy-1,2-propyleneoxy units, and oxyethyleneoxy units, the mole ratio of the latter two types of unit ranging from about 1:10 to about 1:0 as previously noted.

If the optional hydrophilic units, i.e., those additional to the end-capping units, e.g., poly(oxyethylene)oxy units, 5-sulfoisophthaloyl units, or mixtures thereof, are present in the backbone, they generally will comprise at least about 0.05 moles per mole of said ester.

Preferred compositions provided by the invention are well illustrated by one comprising from about 25% to about 100% by weight of ester having the empirical formula $(CAP)_x(EG/PG)_y(T)_z$; wherein (CAP) represents the sodium salt form of said sulfobenzoyl end-capping units (i); (EG/PG) represents said oxyethyleneoxy and oxy-1,2-propyleneoxy units (ii); (T) represents said terephthaloyl units (iii); x is from about 1 to 2; y is from about 2.25 to about 9; z is from about 1.25 to about 8; wherein x, y and z represent the average number of moles of the corresponding units per mole of said ester. More preferably in compositions of this type, the oxyethyleneoxy:oxy-1,2-propyleneoxy mole ratio ranges from about 1:1 to about 7:1; x is about 2, y is from about 2.25 to about 8, and z is from about 1.25 to about 7. Most highly preferred of these ester compositions comprise at least 50% by weight of said ester molecules (oligomers) having molecular weights ranging from about 600 to about 2,000.

In the process aspect of the invention, the invention encompasses the preparation of the aforesaid $(CAP)_x(EG/PG)_y(T)_z$ linear esters by a process most preferably comprising reacting dimethyl terephthalate, ethylene glycol, 1,2-propylene glycol and a compound selected from the group consisting of monovalent cation salts of sulfobenzoic acid and its $C_1$–$C_4$ alkyl carboxylate esters, in the presence of at least one conventional transesterification catalyst. The resulting water-soluble or dispersible ester mixtures are used as fabric soil release materials, the best results being achieved with, but not being limited to, polyester fabrics. Another highly preferred composition herein based on water-soluble or dispersible soil release esters is provided by a process which most preferably comprises reacting dimethyl terephthalate, 1,2-propylene glycol and a compound selected from the group consisting of monovalent cation salts of sulfobenzoic acid and its $C_1$–$C_4$ alkyl carboxylate esters, in the presence of at least one conventional transesterification catalyst.

As disclosed hereinabove, the backbone of the esters herein can optionally be modified by incorporation of hydrophiles such as 5-sulfoisophthaloyl, poly(oxyethylene)oxy, and mixtures thereof. This provides compositions such as those comprising from about 25 to about 100% by weight of ester having the empirical formula $(CAP)_x(EG/PG)_y(T)_z(SIP)_q$ wherein (CAP)

represents the sodium salt form of said sulfobenzoyl end-capping units (i); (EG/PG) represents said oxyethyleneoxy and oxy-1,2-propyleneoxy units (ii); (T) represents said terephthaloyl units (iii); (SIP) represents the sodium salt form of said 5-sulfoisophthaloyl units (iv); x is from about 1 to 2; y is from about 2.25 to about 39; z is from about 1 to about 34; q is from about 0.05 to about 18; wherein x, y, z and q represent the average number of moles of the corresponding units per mole of said ester. Preferred esters of this type with 5-sulfoisophthaloyl units have the oxyethyleneoxy:oxy-1,2-propyleneoxy mole ratio ranging from about 0:1 to about 7:1; x is from about 1 to 2, y is from about 3 to about 39, z is from about 1 to about 34, and q is from about 1 to about 18, and more preferably have x of about 2, y of about 14, z of about 11 and q of about 2. Excellent soil release compositions are those wherein at least about 50% by weight of said ester has a molecular weight ranging from about 800 to about 20,000. In a preferred synthesis and composition in accordance with the above-defined numbers of units, water-soluble or dispersible ester mixtures are prepared by reacting dimethyl terephthalate, ethylene glycol, 1,2-propylene glycol, a dimethyl-5-sulfoisophthalate monovalent cation salt and a compound selected from the group consisting of monovalent cation salts of sulfobenzoic acid and its $C_1$-$C_4$ alkyl carboxylate esters, in the presence of at least one conventional transesterification catalyst.

Following the same empirical nomenclature, when poly(oxyethylene)oxy units are optionally present in the backbone, the ester mixtures herein will comprise from about 25 to about 100% by weight of ester having the empirical formula $(CAP)_x(EG/PG)_y(T)_z(E_n)_r$ wherein (CAP) represents the sodium salt form of said sulfobenzoyl end-capping units (i); (EG/PG) represents said oxyethyleneoxy and oxy-1,2-propyleneoxy units (ii); (T) represents said terephthaloyl units (iii); $(E_n)$ represents said poly(oxyethylene)oxy units (v), which are further characterized in having an average degree of ethoxylation which ranges from 2 to about 100; x is from about 1 to 2; y is from about 2.25 to about 39; z is from about 1.25 to about 34; r is from about 0.05 to about 10; wherein x, y, z and r represent the average number of moles of the corresponding units per mole of said ester. Preferably in such compositions, the oxyethyleneoxy:oxy-1,2-propyleneoxy mole ratio of said units (ii) ranges from about 0:1 to about 7:1; x is about 2, y is from about 2.25 to about 17, z is from about 1.75 to about 18 and r is from about 0.5 to about 2. More preferably, in such esters, x is about 2, y is from about 4 to about 8, z is from about 4 to about 8, r is about 1 and n is from about 30 to about 85 (more preferably, about 60 to about 85; most preferably about 77). Most preferably, such ester mixtures are comprised of at least about 50% by weight of said ester having molecular weight ranging from about 2,000 to about 12,000. In a preferred synthesis and composition in accordance with the above-defined numbers of units, water-soluble or dispersible ester mixtures are prepared by a process which comprises reacting dimethyl terephthalate, ethylene glycol, 1,2-propylene glycol, a polyoxyethylene glycol having an average degree of ethoxylation ranging from about 30 to about 85, and a compound selected from the group consisting of monovalent cation salts of sulfobenzoic acid and its $C_1$-$C_4$ alkyl carboxylate esters, in the presence of at least one conventional transesterification catalyst.

While it is undesirable to introduce hydrophiles such as 5-sulfoisophthalate and poly(oxyethylene)oxy into the esters to an extent which would prevent deposition of the esters when used as soil release agents, it is possible to combine these anionic and nonionic hydrophiles in the ester backbones. Thus, the invention also provides ester compositions comprising from about 25 to about 100% by weight of ester having the empirical formula $(CAP)_x(EG/PG)_y(T)_z(SIP(_q(E_n)_r$ or $(CAP)_x(PG)_y(T)_z(SIP)_q(E_n)_r$ wherein (CAP), (EG/PG0 etc., are as defined hereinabove, x is from about 1 to about 2, y is from about 2.25 to about 39, z is from about 1 to about 34, q is from about 0.05 to about 18, r is from about 0.05 to about 10 and n is from 2 to about 100, the sum of q+r being a number preferably not in excess of about 20.

All percentages herein are given, unless expressly otherwise indicated, on a weight basis.

DETAILED DESCRIPTION OF THE INVENTION

The present invention encompasses novel compositions suitable for use in consumer fabric care products such as granular detergents, dryer-added sheet fabric softeners. The essential component of the compositions is a particular kind of ester, characterized by certain essential end-capping units as well as other essential units, all in particular proportions and having structural arrangements as described hereinafter.

The esters herein can be simply characterized as oligomers or relatively low molecular weight polymers which comprise a substantially linear ester "backbone" and end-capping units which are sulfo-aroyl, especially sulfobenzoyl. Proper selection of the structural units which comprise the ester backbone and use of sufficient amounts of the sulfo-aroyl end-capping units results in the desired soil-release properties of these materials.

Oligomeric/Polymeric Esters—It is to be understood that the compositions herein are not resinous, high molecular weight, macromolecular or fiber-forming polyesters, but instead are relatively low molecular weight and contain species more appropriately described as oligomers rather than as polymers. Individual ester molecules herein can have molecular weights ranging from about 500 to about 20,000, esters containing the above-defined optional units predominantly accounting for weights at the high end of this range. (Polymeric, non-polyester units such as poly(oxyethylene)oxy, are typical of the optional units which increase the molecular weights of the esters). Relevant for purposes of comparison with glycol-terephthalate fibrous polyesters (typically averaging 30,000 or more in molecular weight) is the molecular weight range from about 500 to about 2,000, within which molecules of the preferred esters of the invention which incorporate only the essential units are generally found. Accordingly, the compositions of this invention are referred to as "oligomeric or polymeric esters" rather than "polyester" in the colloquially used sense of that term as commonly used to denote high polymers such as fibrous polyesters.

Molecular Geometry—The esters of the invention are all "substantially linear", in the sense that they are not significantly branched or crosslinked by virtue of the incorporation into their structure of units having more than two ester-bond forming sites. (For a typical example of polyester branching or crosslinking of the type excluded in defining esters of the present invention, see Sinker et al, U.S. Pat. No. 4,554,328, issued Nov. 19, 1985.) Furthermore, no cyclic esters are essential for the purposes of the invention, but may be present in the compositions of the invention at low levels as a result of side-reactions during ester synthesis. Preferably, cyclic esters will not exceed about 2% by weight of the compositions; most preferably, they will be entirely absent from the compositions.

Contrasting with the above, the term "substantially linear" as applied to the esters herein does, however, expressly encompass materials which contain side-chains which are unreactive in ester-forming or transesterification reactions. Thus, oxy-1,2-propyleneoxy. units are of an unsymmetrically substituted type essential in the preferred embodiment; their methyl groups do not constitute what is conventionally regarded as "branching" in polymer technology (see Odian, Principles of Polymerization, Wiley, N.Y., 1981, pages 18–19, with which the present definition are fully consistent), are unreactive in ester-forming reactions, and are highly desirable for the purposes of the invention as will be seen from the disclosures hereinafter. Optional units in the esters of the invention can likewise have side-chains, provided that they conform with the same nonreactivity criterion.

Molecular Units The esters of this invention comprise repeating backbone units, and end-capping units. To briefly illustrate, in the preferred embodiment of the invention molecules of the ester are comprised of three kinds of essential units, namely (i) sulfobenzoyl end-capping units of the formula $(MO_3S)(C_6H_4)C(O)-$ wherein M is a salt-forming cation;

(ii) oxy-1,2-propyleneoxy units, i.e., $-OCH_2CH(CH_3)CH_2O-$ or $-OCH_2CH(CH_3)O-$, or mixtures thereof with oxyethyleneoxy units, i.e., $-OCH_2CH_2O-$. Note that the latter units are defined as excluding oxyethyleneoxy units which are connected together to form a poly(oxyethylene)oxy chain comprising two or more consecutive oxyethylene units; and (iii) terephthaloyl units, i.e., $-(O)CC_6H_4C(O)-$; note that as generally used herein, the latter formula is indicative of a

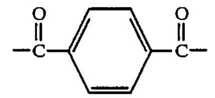

unit.

Optionally, the esters herein may also, in addition to units of types (i)–(iii), contain hydrophilic units, which can be nonionic or anionic in character. These units most preferably are (iv) 5-sulfoisophthaloyl units of the formula $-(O)C(C_6H_3)(SO_3M)C(O)-$ wherein M is a salt-forming cation; and (v) poly(oxyethylene)oxy units of the formula $-(OCH_2CH_2)_nO-$ wherein the average degree of ethoxylation n ranges from 2 to about 100.

Combinations of the optional units are also acceptable, as in:

(vi) a mixture of said units (iv) and (v), at particular (iv):(v) mole ratios.

The following structures are illustrative of structures of ester molecules falling within the foregoing preferred and optional embodiments, and demonstrate how the units are connected:

(a) doubly end-capped ester molecule comprised of the essential units (i), (ii) and (iii);

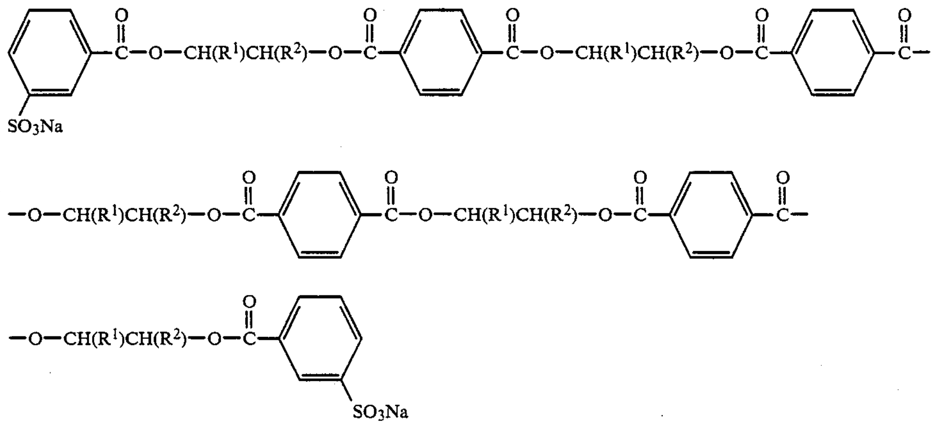

(b) singly end-capped ester molecule comprised of essential units (i), (ii) and (iii);

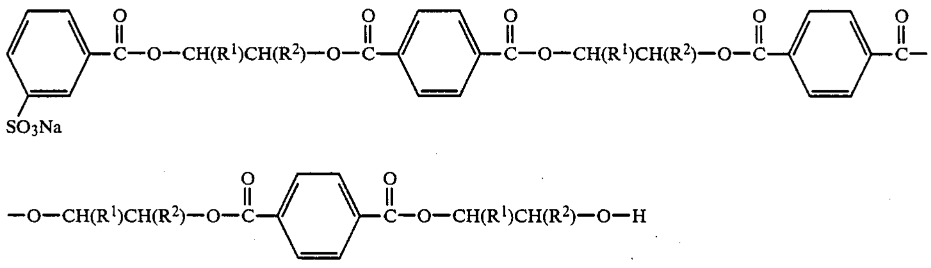

(c) doubly end-capped ester molecule, (termed a "hybrid backbone" ester molecule herein) comprised of

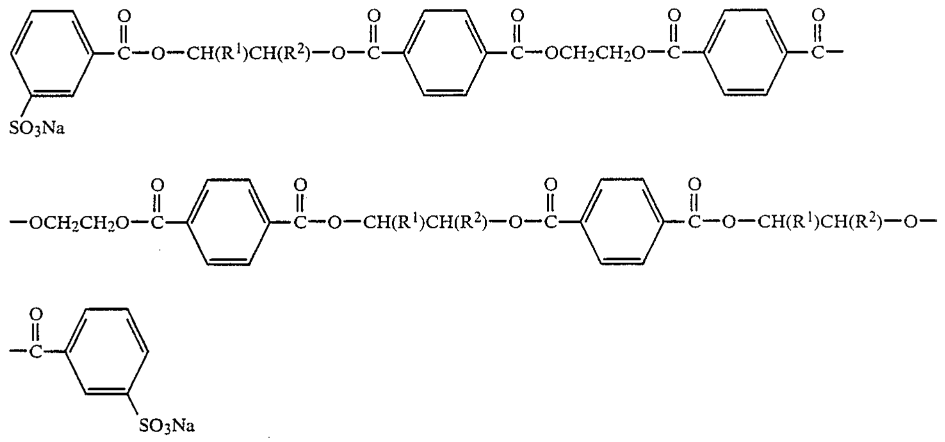

essential units (i), (ii) and (iii); units (ii) being a mixture of oxyethyleneoxy and oxy-1,2-propyleneoxy units, in the example shown below at a 2:3 mole ratio (on average, in ester compositions as a whole in contrast to individual molecules such as illustrated here, ratios ranging from about 5:1 to about 2:1 are the most highly preferred when the compositions are based on the units (i), (ii) and (iii));

(d) doubly end-capped ester molecule comprised of essential units (i), (ii) and (iii), together with an optional unit (iv);

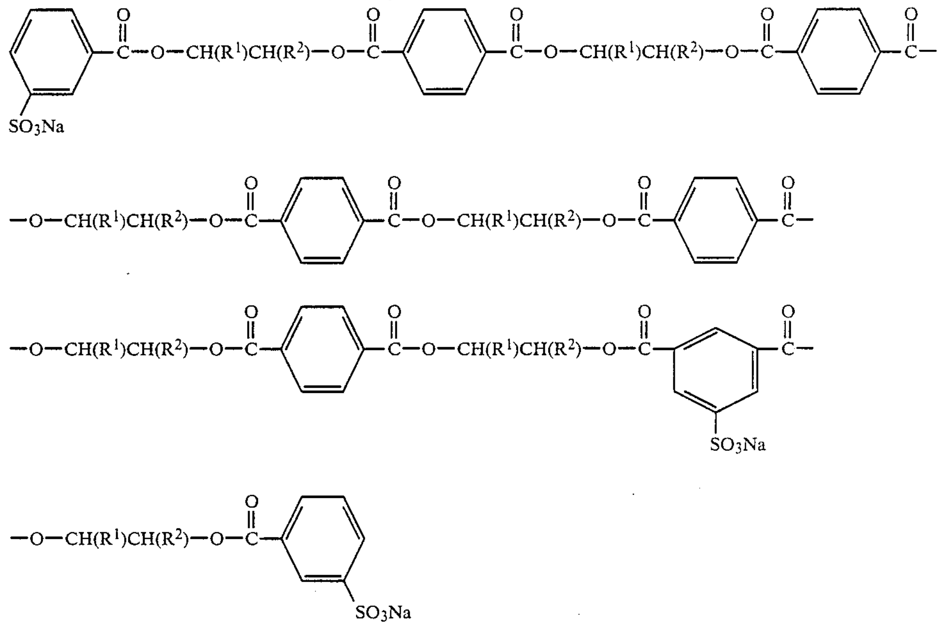

(e) singly end-capped ester molecule comprised of essential units (i), (ii) and (iii), together with optional units (v);

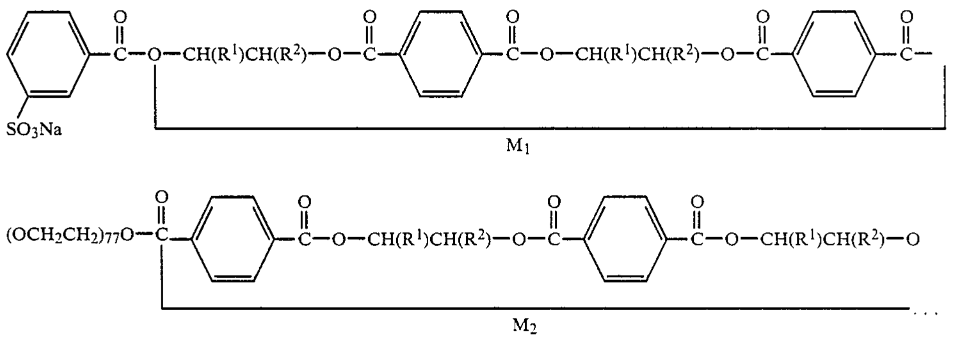

-continued

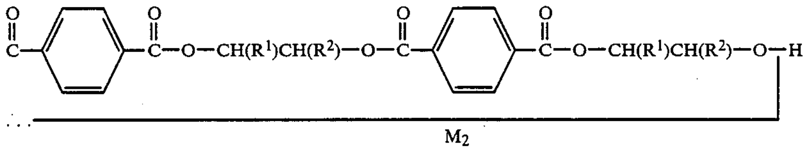

(f) doubly end-capped ester molecule comprised of essential units (i), (ii), (iii), and optional units (v);

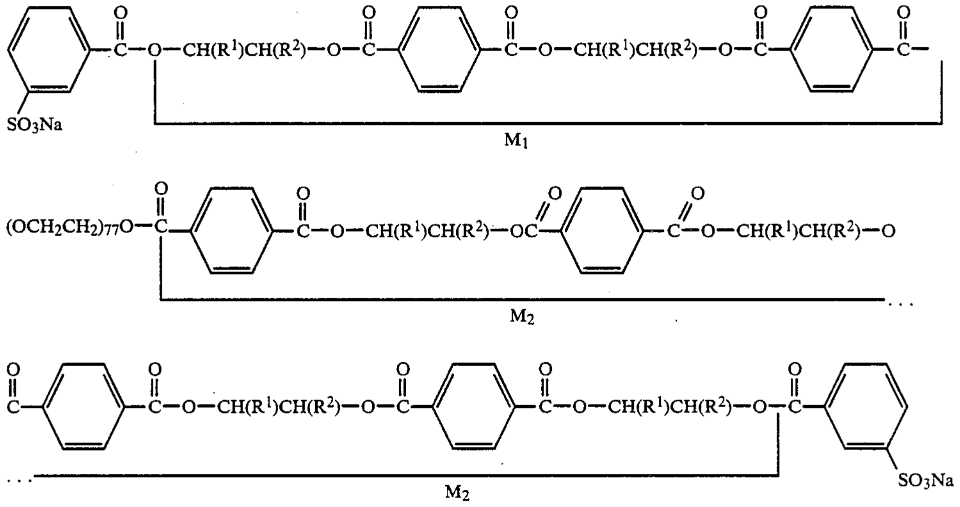

In all of structures (a)-(f), $R^1$ and $R^2$ are selected so that $R^1$ or $R^2$ is randomly —$CH_3$, with the second R group of each —$OCH(R^1)CH(R^2)O$— unit in each instance being —H.

Returning to the invention are more broadly defined, it will be seen from the above disclosure that the units essential for the invention are individually art-recognized. Despite this fact, the new arrangement of units upon which the invention is based, leads to ester molecules and ester-containing compositions hitherto unkown and exceptionally useful in the field of the present invention.

In the context of the structures of ester molecules disclosed herein, it should be recognized that the present invention encompasses not only the arrangement of units at the molecular level, but also in each instance the gross mixtures of esters which result from the reaction schemes herein, and which have the desired range of composition and properties. Accordingly, the "esters of the invention" is a term which encompasses the novel doubly and singly end-capped compounds disclosed herein, mixtures thereof, and mixtures of said end-capped materials which may unavoidably contain some non-capped species, although levels of the latter will be zero or at a minimum in all of the highly preferred compositions.

Thus, when referring simply to an "ester" herein, it is furthermore intended to refer, by definition, collectively to the mixture of sulfo-aroyl capped and the uncapped ester molecules resulting from any single preparation.

Ester Backbone—To further illustrate this point, consider esters of the invention comprised exclusively of the- essential terephthaloyl and oxy-1,2-propyleneoxy units and the sulfo-aroyl end-capping units. In molecules of this ester, the oxy-1,2-propyleneoxy and terephthaloyl units are connected in alternation, forming the ester backbone.

Groups at the Termini of the Ester Backbone

Any ester molecules which are present in compositions of the invention which are not fully, i.e., doubly, end-capped by the end-capping units, must terminate with units which are not sulfoaroyl end-capping units. These termini will be hydroxyl groups or other groups attributable to the unit-forming reactant. For example, the following molecule: $NaO_3SC_6H_4$-$C(O)$—$OCH_2CH(CH_3)O$—$(O)CC_6H_4$-$C(O)$—$OCH(CH_3)CH_2OH$ contains, from left to right, one sulfobenzoyl end-capping unit, one oxy-1,2-propyleneoxy unit, one terephthaloyl unit, and one oxy-1,2-propyleneoxy unit in a chain terminal position to which is attached —H forming a hydroxyl group. In other examples which may be constructed, units such as —$(O)CC_6H_4C(O)$—$OCH_3$ may be found in terminal positions. All the most highly preferred ester molecules herein will, however, as indicated above, have two sulfo-aroyl end-capping units and no residual units occupying terminal positions; for example: $NaO_3SC_6H_4$-$C(O)$—$OCH_2CH(CH_3)O$—$(O)CC_6H_4$-$C(O)$—$OCH(CH_3)CH_2O$—$(O)CC_6H_4SO_3Na$.

Symmetry

It is to be appreciated that in the above formulas the oxy-1,2-propyleneoxy units can have their methyl groups randomly alternating with one of the adjacent —$CH_2$- hydrogen atoms, thereby lowering the symmetry of the ester chain. Thus, the first oxy-1,2-propyleneoxy. unit in the formula immediately above is depicted as having the —$OCH_2CH(CH_3)O$— orientation, while the second such unit has the opposite, —$OCH(CH_3)CH_2O$— orientation. Carbon atoms in the oxy-1,2-propylene units, to which atoms the methyl groups are attached, are furthermore asymmetric, i.e., chiral; they generally have four nonequivalent chemical entities attached. Contrasting with the oxy-1,2-propyleneoxy units, oxyethyleneoxy units cannot be used herein as a sole source of oxy-1,2-alkyleneoxy units since they lack the unsymmetrical character which is needed. On the other hand, esters of the invention can satisfactorily be prepared having structures in which all oxy-1,2-propyleneoxy units are replaced with their higher oxy-1,2-alkyleneoxy homologs, ethyl, n-propyl and n-butyl io or similar groups either fully or partially replacing the methyl side-chains of oxy-1,2-propyleneoxy units.

Fabric Substantivity and Formulability of the Esters

The ester backbone provides fabric substantivity of the compositions herein. In a preferred embodiment, alternating terephthaloyl and oxy-1,2-propyleneoxy units form an ester backbone which is not only fabric substantive, but also very compatible with consumer fabric care ingredients. As noted hereinabove, units having R— sidechains alternative to the $R{=}CH_3$ sidechains of the oxy-1,2-propyleneoxy units can be substituted for the oxy-1,2-propyleneoxy units, for the purposes of utilizing the broader aspects of the invention. However, these alternative units must have crystallinity-disruptive effects without either excessively decreasing polyester fabric substantivity or enhancing interactions undesirable from the perspective of consumer product formulation (such as by enhancing interactions with detergents in a detergent product); examples of such units include those in which the methyl group as found in oxy-1,2-propyleneoxy units, is replaced by groups such as ethyl or methoxymethyl. However, for the purposes of consumer product compatibility, economy as well as effectiveness, no unit preferable to the oxy-1,2-propyleneoxy units as a direct replacement has been identified.

Fabric substantivity to polyesters can, as shown by soil release technical tests, be further enhanced by using oxyethyleneoxy units in addition to the above-defined unsymmetrical oxy-1,2-alkyleneoxy units (a) or (b) herein. However, the use of units which are exclusively oxyethyleneoxy units in replacement of all the unsymmetrical oxy-1,2-alkyleneoxy units is not in accordance with the invention. (Surprisingly, the esters then do not result in good soil release agents for the purposes herein, especially in that they are ill-suited to formulation-in consumer products by comparison with the esters of the invention). Accordingly, the compositions herein all essentially contain some significant proportion of the unsymmetrical oxy-1,2-alkyleneoxy units, especially oxy-1,2-propyleneoxy units.

Various optional units of a hydrophilicity-enhancing and nonpolyester substantive type can be incorporated into the esters. The pattern of such incorporation will generally be random. Preferred optional units are anionic hydrophiles, such as 5-sulfoisophthaloyl, and nonionic hydrophiles, such as poly(oxyethylene)oxy or similar units. Such units will, when incorporated into the ester backbone, divide it into two or more hydrophobic moieties separated by one or more hydrophilic moieties. Structures (e) and (f) hereinabove are illustrative of ester molecules having two hydrophobic moieties ($M_1$ and $M_2$) separated by one, hydrophilic, poly-(oxyethylene)oxy moiety. Without intending to be limited by theory, it is believed that in the above examples (e) and (f), the $M_2$ moieties are especially polyester-fabric substantive.

It should also be noted that the essential non-charged aryldicarbonyl units herein need not exclusively be terephthaloyl units, provided that the polyester-fabric-substantivity of the ester is not harmed to a significant extent. Thus, for example, minor amounts of isomeric non-charged dicarbonyl units, such as isophthaloyl or the like, are acceptable for incorporation into the esters.

End-Capping Units

The end-capping units used in the esters of the present invention are sulfo-aroyl groups. These end-cap units provide anionic charged sites when the esters are dispersed in aqueous media, such as a laundry liquor or rinse bath. The end-caps serve to assist transport in aqueous media, as well as to provide hydrophilic sites on the ester molecules which are located for maximum effectiveness of the esters as soil release agents.

Suitable end-capping units herein generally have calculated molecular weights from about 190 to about 500, and are preferably selected to avoid high degrees of crystallinity of the overall ester molecule. Sulfobenzoyl end-capping units are- preferred, and can exist as isomers with the sulfonate substituent at the ortho-, meta- or para- positions with respect to the carbonyl substituent. Sulfobenzoyl isomer mixtures and pure metasulfobenzoyl substituents are among the most highly preferred end-capping units, whereas pure para-isomers are significantly less desirable, especially when the esters are at the low end of the specified molecular weight range or when the ratio of unsymmetrical oxy-1,2-alkyleneoxy to oxyethyleneoxy units is low. It is highly preferred that not more than about 0.15 mole fraction of the sulfobenzoyl end-capping units be in para-form, or that exclusively ortho- or meta-sulfobenzoyl end-capping units should be used. Of the highly preferred forms, industrially prepared sulfobenzoyl isomer mixtures having controlled paraisomer content are most economical. It is also noted that such isomer mixtures may contain up to 0.1 mole fraction of benzoic acid or similar unsulfonated material, without ill effects; higher levels of unsulfonated material are in certain instances more likely to be tolerated, e.g., when the molecular weights of the esters are low.

The sulfobenzoyl end-capping units herein have the formula $(MO_3S\ )(C_6H_4)C(O)$— wherein M is a salt-forming cation. It is not intended to exclude the acid form, but most generally the esters herein are used as sodium salts, as salts of other alkali metals, as salts with nitrogen-containing cations (especially tetraalkylammonium), or as the disassociated anions in an aqueous environment.

On a mole basis, the compositions herein will preferably comprise from about one to about two moles of the sulfoaroyl end-capping units per mole of the ester. Most preferably, the esters are doubly end-capped; i.e., there will be two moles of end-capping units present per mole of the esters. From the viewpoint of weight composition, it will be clear that the contribution of end-capping units to the molecular weight of the esters will decrease as the molecular weight of the ester backbone increases.

Method for Making Sulfoaroyl End-Capped Esters

The ester compositions of the present invention can be prepared using any one or combination of several alternative general reaction types, each being well-known in the art. Many different starting materials and diverse, well-known experimental and analytical techniques are useful for the syntheses. Types of synthetic and analytical methods useful herein are well illustrated in European Patent Application No. 185,427, Gosselink, published June 25, 1986, and in Odian, Principles of Polymerization, Wiley, N.Y., 1981, both of which are incorporated herein by reference. Chapter 2.8 of the Odian reference, entitled "Process Conditions", pp 102–105, focuses on the synthesis of poly(ethylene terephthalate); it should be noted that the synthesis temperatures reported in Odian (260°–290° C.) are unsuitably high for general use herein; also that the use of two types of catalyst, the first being deactivated by means of a phosphorus compound before use of the second, is not necessary herein. Temperature requirements and catalysts for use herein are further discussed hereinafter.

Mechanistically, the suitable general reaction types for preparing esters of the invention include those classifiable as:

1. alcoholysis of acyl halides;
2. esterification of organic acids;
3. alcoholysis of esters (transesterification); and
4. reaction of alkylene carbonates with organic acids.

Of the above, reaction types 2–4 are highly preferred since they render unnecessary the use of expensive solvents and halogenated reactants. Reaction types 2 and 3 are especially preferred as being the most economical.

Suitable starting materials or reactants for making the esters of this invention are any reactants (especially esterifiable or transesterifiable reactants) which are capable of combining in accordance with the reaction types 1–4, or combinations thereof, to provide esters having the correct proportions of all the above-specified units (i) to (v) of the esters.

Such reactants can be categorized as "simple" reactants, i.e., those which are singly capable of providing only one kind of unit necessary for making the esters; or as derivatives of the simple reactants which singly contain two or more different types of unit necessary for making the esters. Illustrative of the simple kind of reactant is dimethyl terephthalate, which can provide only terephthaloyl units. In contrast, bis(2-hydroxypropyl)terephthalate is a reactant which can be prepared from dimethyl terephthalate and 1,2-propylene glycol, and which can desirably be used to provide two kinds of unit, viz. oxy-1,2propyleneoxy and terephthaloyl, for making the esters herein. Similarly, compounds such as

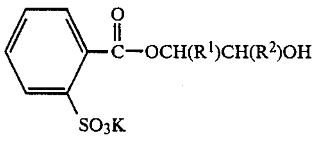

(I)

and

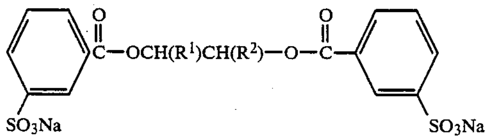

(II)

, wherein $R^1$, $R^2$=H or $CH_3$ (provided that when $R^1$=H, $R^2$=$CH_3$ and when $R^2$=H, $R^1$=$CH_3$), could be used to provide both endcapping (sulfobenzoyl) and oxy-1,2-propyleneoxy units. In principle it is also possible to use oligoesters, or polyesters such as poly(1,2-propylene terephthalate), as reactants herein, and to conduct transesterification with a view to incorporation of end-capping units while decreasing molecular weight, rather than following the more highly preferred procedure of making the esters from the simplest reactants in a process involving molecular weight increase (to the limited extent provided for by the invention) and end-capping.

Since "simple" reactants are those which will most preferably and conveniently be used, it is useful to illustrate this kind of reactant in more detail. Thus, aromatic sulfocarboxylates, in acid (generally neutralized to place the sulfonate group in salt form prior to continuing synthesis), carboxylate-salt or carboxylate-lower (e.g. $C_1$–$C_4$) alkyl ester forms such as (III), can be used as the source of the essential end-capping units herein;

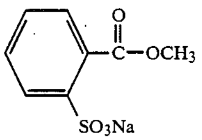

(III)

additional examples of such reactants are m-sulfobenzoic acid and m-sulfobenzoic acid monosodium salt. (Note that in (I)–(III) above, the metal cation can be replaced by potassium or a nitrogen-containing cation provided that the latter is unreactive during the synthesis, e.g. tetraalkylammonium. It is, of course possible to subject any of the esters of the invention to cation exchange after the synthesis, thereby affording a means of introducing more esoteric or reactive cations into the ester compositions). The cyclic anhydride of o-sulfobenzoic acid is likewise suitable as a "simple" reactant herein, though less preferred than the above-named acids and esters of sulfobenzoic acid. Mixtures of sulfobenzoate isomers can be used, provided that not more than about 0.15 mole fraction of the isomers are in para-form. If commercial grades of sulfoaroyl end-capping reactants are used, the content of unsulfonated material, such as benzoic acid or the like, should not exceed about 0.1 mole fraction of the reactant for best results. Mineral acids such as sulfuric acid or oleum will be removed from the sulfonated reactant before use. Water can be present, e.g., as in crystal hydrates of the sulfoaroyl end-capping reactant, but will not desirably constitute a large proportion thereof.

Appropriate glycols or cyclic carbonate derivatives thereof can be used to provide the essential oxy-1,2-alkyleneoxy units; thus, 1,2-propylene glycol (preferred especially on grounds of its lower cost) or (where the starting carboxyl groups are present in an acidic form) the cyclic carbonate

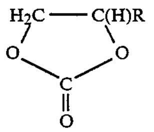

(IV)

(R=methyl, ethyl, n-propyl, n-butyl) are suitable sources of oxy-1,2-alkyleneoxy units for-use herein. Compounds (IV) having the essential oxy-1,2-alkyleneoxy moieties oxy-1,2-butyleneoxy, oxy-1,2-pentyleneoxy and oxy-1,2-hexyleneoxy, respectively, are the cyclic carbonates 4-ethyl-1,3-dioxolan-2-one, 4-n-propyl-1,3-dioxolan-2-one, and 4-n-butyl-1,3-dioxolan-2-one. Fagerburg, J. Appl. Polymer Sci., Vol. 30, 889–896 (1985), which is incorporated herein by reference, gives preparative details for these compounds. Oxyethyleneoxy units, which are sometimes also present in the esters of the invention, are most conveniently provided by ethylene glycol, though as an alternative, ethylene carbonate could be used when free carboxylic acid groups are to be esterified.

Aryldicarboxylic acids or their lower alkyl esters can be used to provide the essential aryldicarbonyl units; thus, terephthalic acid or dimethyl terephthalate are suitable sources of terephthaloyl units. In general, it is preferred herein to use ester, rather than acid forms of reactants which provide the aryldicarbonyl units.

Units of the esters, which are optional in the invention as broadly defined, will be provided by well-known and readily identifiable reagents; for example, polyethylene glycols, such as PEG-3400 (degree of ethoxylation=about 77), are a suitable source of poly(oxyethylene)oxy units for use herein; and dimethyl-5-sulfoisophthalate, sodium salt, is an example of a reagent capable of providing 5-sulfoisophthaloyl units for optional incorporation into the esters of the invention. It is generally preferred that all units of the types (iv) and (v) defined hereinabove should be provided by reactants in ester or alcohol forms.

When starting with the simplest reactants as illustrated above, the overall synthesis is usually multi-step, involving at least two stages, such as an initial esterification or transesterification (also known as ester interchange) stage, followed by an oligomerization or polymerization stage, in which molecular weights of the esters are increased, but only to a limited extent as provided for by the invention.

Formation of ester-bonds in reaction types 2 and 3 involves elimination of low molecular weight by-products such as water (reaction 2), or simple alcohols (reaction 3). Complete removal of the latter from reaction mixtures is generally somewhat easier than removal of the former. However, since the ester-bond forming reactions are generally reversible, it is necessary to "drive" the reactions forward in both instances, removing these by-products.

In practical terms, in the first stage (ester interchange) the reactants are mixed in appropriate proportions and are heated, to provide a melt, at atmospheric or slightly superatmospheric pressures (preferably of an inert gas such as nitrogen or argon). Water and/or low molecular weight alcohol is liberated and is distilled from the reactor at temperatures up to about 200° C. (A temperature range of from about 150°–200° C. is generally preferred for this stage).

In the second (i.e., oligomerization) stage, vacuum or inert gas sparging techniques and temperatures somewhat higher than in the first stage are applied; removal of volatile by-products and excess reactants continues, until the reaction is complete, for example as monitored by conventional spectroscopic techniques. (Inert gas sparging which can be used in this stage involves forcing an inert gas, such as nitrogen or argon, through the reaction mixture to purge the reaction vessel of the abovementioned volatiles; in the alternative, continuously applied vacuum, typically of about 10 mm Hg or lower can be used; the latter technique is preferred especially when high viscosity melts are being reacted).

In both of the above-described reaction stages, it is necessary to balance on one hand the desire for rapid and complete reaction (higher temperatures and shorter times preferred), against the need to avoid thermal degradation (which undesirably might result in off-colors and by-products). It is possible to use generally higher reaction temperatures especially when reactor design minimizes super-heating or "hot spots"; also, ester-forming reactions in which ethylene glycol (rather than exclusively 1,2-propylene or higher glycols) is present, are more tolerant of higher temperatures. Thus, a suitable-temperature for oligomerization lies most preferably in the range of from about 150° C. to about 260° C. when ethylene glycol is present and in the range of from about 150° C. to about 240° C. when it is absent (assuming that no special precautions, such as of reactor design, are otherwise taken to limit thermolysis).

It is very important in the above-described procedure to use continuous mixing, so that the reactants are always in good contact; highly preferred procedures involve formation of a well-stirred homogeneous melt of the reactants in the temperature ranges given above. It is also highly preferred to maximize the surface area of reaction mixture which is exposed to vacuum or inert gas to facilitate the removal of volatiles, especially in the oligomerization or polymerization step; mixing equipment of a high-shear vortex-forming type and gas spargers giving good gas-liquid contact are best suited for this purpose.

Catalysts and catalyst levels appropriate for esterification, transesterification, oligomerization, and for combinations thereof, are all well-known in polyester chemistry, and will generally be used herein; as noted above, a single catalyst will suffice. Suitably catalytic metals are reported in Chemical Abstracts, CA83:178505v, which states that the catalytic activity of transition metal ions during direct esterification of K and Na carboxybenzenesulfonates by ethylene glycol decreases in the order Sn (best), Ti, Pb, Zn, Mn, Co (worst).

The reactions can be continued over periods of time sufficient to guarantee completion, or various conventional analytical monitoring techniques can be employed to monitor progress of the forward reaction; such monitoring makes it possible to speed up the procedures somewhat, and to stop the reaction as soon as a product having the minimum acceptable composition is formed.

Appropriate monitoring techniques include measurement of relative and intrinsic viscosities, acid values, hydroxyl numbers, $^{1}H$ and $^{13}C$ nuclear magnetic resonance (n.m.r) spectra, and liquid chromatograms.

Most conveniently, when using a combination of volatile reactants (such as a glycol) and relatively involatile reactants (such as m-sulfobenzoic acid and dimethyl terephthalate), the reaction will be initiated with excess glycol being present. As in the case of ester interchange reactions reported by Odian (op. cit.), "stoichiometric balance is inherently achieved in the last stages of the second step of the process". Excess glycol can be removed from the reaction mixture by distillation; thus, the exact amount used is not critical.

Inasmuch as final stoichiometry of the ester compositions depends on the relative proportions of reactants retained in the reaction mixtures and incorporated into the esters, it is desirable to conduct the condensations in a way which effectively retains the non glycol reactants, and prevents them from distilling or subliming.

Dimethylterephthalate and to a lesser extent the simple glycol esters of terephthalic acid have sufficient volatility to show on occasion "sublimation" to cooler parts of the reaction apparatus. To ensure achieving the desired stoichiometry it is desirable that this sublimate be returned to the reaction mixture, or alternatively, that sublimation losses be compensated by use of a small excess of terephthalate. In general, sublimation-type losses, such as of dimethyl terephthalate, may be minimized (1) by apparatus design; (2) by raising the reaction temperature slowly enough to allow a large proportion of dimethyl terephthalate to be converted to less volatile glycol esters before reaching the upper reaction temperatures; (3) by conducting the early phase of the transesterification under low to moderate pressure (especially effective is a procedure allowing sufficient reaction time to evolve at least about 90% of the theoretical yield of methanol before applying vacuum or strong sparging). On the other hand the "volatile" glycol components used herein must be truly volatile if an excess is to be used. In general, lower glycols or mixtures thereof having boiling points below about 350° at atmospheric pressure are used herein; these are volatile enough to be practically removable under typical reaction conditions.

Typically herein, when calculating the relative proportions of reactants to be used, the following routine is followed, as illustrated for a combination of the reactants m-sulfobenzoic acid monosodium salt (A), 1,2-propylene glycol (B) and dimethylterephthalate (C):

1. the desired degree of end-capping is selected; for the present example, the value 2, most highly preferred according to the invention, is used;
2. the average calculated number of terephthaloyl units in the backbone of the desired ester is selected; for the present example, the value 3.75, which falls in the range of most highly preferred values according to the invention, is used;
3. the mole ratio of (A) to (B) should thus be 2:3.75; amounts of the reactants (A) and (B) are taken accordingly;
4. an appropriate excess of glycol is selected; typically 2 to 10 times the number of moles of dimethyl terephthalate is suitable.

More generally herein, when preparing fully end-capped ester from "simple" reactants, a ratio of the moles of end-capping reactant to moles of all other nonglycol organic reactants (e.g., in the simplest case only dimethyl terephthalate) of from about 2:1 to about 1:20, most preferably about 1:1 to about 1:5 will be used. The glycol used will be calculated in an amount, in any event sufficient to allow interconnection of all other units by means of ester bonds, and adding a convenient excess will usually result in a total relative amount of glycol ranging from about 1.5 to about 10 moles for each mole nonglycol organic reactants added together.

In light of the teaching of the present invention (insofar as the identity and proportions of essential end-capping and backbone units are concerned), numerous syntheses of ester compositions according to the invention follow straightforwardly from the above disclosure. The following, more detailed examples are illustrative.

EXAMPLE I

An ester composition made from m-sulfobenzoic acid monosodium salt, 1,2-propylene glycol, and dimethyl terephthalate. The example illustrates a generally useful synthesis of preferred doubly end-capped esters of the invention.

Into a 500 ml, three-necked, round bottom flask, fitted with a thermometer, magnetic stirrer and modified Claisen head, the latter connected to a condenser and receiver flask, are placed, under argon, m-sulfobenzoic acid monosodium salt (50.0 g; 0.22 moles; Eastman Kodak), 1,2-propylene glycol (239.3 g; 3.14 moles; Fisher), and hydrated monobutyltin(IV) oxide (0.8 g; 0.2% w/w; sold as FASCAT 4100 by M&T Chemicals). Over a 2 hour period, the mixture is stirred and heated under argon at atmospheric pressure, to reach a temperature of 175° C. The reaction conditions are kept constant for an additional 16 hours, during which time distillate (4.0 g; 100% based on the theoretical yield of water) is collected. The reaction mixture is cooled to about 130° C., and dimethyl terephthalate (79.5 g; 0.41 moles; Aldrich) is added under argon. Over a 7 hour period, the mixture is stirred and heated under argon at atmospheric pressure, to reach a temperature of 175° C. The reaction conditions are kept approximately constant (temperature range 175°-180° C.) for a further 16 hours, during which time distillate (28.7 g; 110% of theory based on the calculated yield of methanol) is collected. The mixture is cooled to about 50° C. and is transferred under argon to a Kugelrohr apparatus (Aldrich). The apparatus is evacuated to a pressure of 1 mm Hg. While maintaining the vacuum and stirring, the temperature is raised to 200° C. over 1.5 hours. Reaction conditions are then held constant for about 8 hours to allow completion of the synthesis. During this period, excess glycol distills from the homogeneous mixture. (In an alternative procedure, the reaction is monitored by sampling and analysis at regular intervals, making it possible to conclude the synthesis more rapidly, the last step taking only 4 hours.)

In referring to the ester compositions of this and the following examples, the following conventions will be used:

| | | |
|---|---|---|
| (CAP) = | sulfoaroyl end-capping units | (i) |
| (PG) = | oxy-1,2-propyleneoxy units | (ii) |
| (EG/PG) = | mixture of oxyethyleneoxy and oxy-1,2-propyleneoxy units | (ii) |
| (2G) = | oxy-1,2-butyleneoxy units | (ii) |
| (3G) = | oxy-1,2-pentyleneoxy units | (ii) |
| (4G) = | oxy-1,2-hexyleneoxy units | (ii) |
| (T) = | terephthaloyl units | (iii) |
| (SIP) = | 5-sulfoisophthaloyl units | (iv) |
| ($E_n$) = | poly(oxyethylene)oxy units, average degree of ethoxylation = n | (v) |

To illustrate the use of the convention, the known compound bis(2-hydroxypropyl) terephthalate of structure:

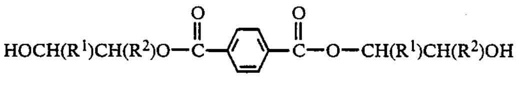

wherein $R^1$, $R^2$=H or $CH_3$ (provided that when $R^1$=H, $R^2$=$CH_3$ and when $R^2$=H, $R^1$=$CH_3$, is structurally represented as:

H—(PG)—(T)—(PG)—H

So as to be able to show the essential units and the number of each as briefly as possible, the structural representation of the same compound is further abbreviated using the empirical formula representation:

$(PG)_2(T)_1$

It will be understood that simple nonessential groups, such as alcohol —H (in the above example), or methyl ester —$CH_3$, can be present in molecules which do not have two end-capping units.

Using the convention, the doubly end-capped ester composition of Example I has the empirical formula:

$(CAP)_2(PG)_{4.75}(T)_{3.75}$ wherein (CAP) represents m-sulfobenzoyl end-capping units in sodium salt form.

Illustrative of structures of individual oligomeric ester molecules of the Example I ester composition are:

(CAP)—(PG)—(T)—(PG)—(T)—(PG)—(T)—(PG)—(CAP), (CAP)—(PG)—(T)—(PG)—(T)—(PG)—(T)—(PG)—(T)—(PG)—(CAP), and (CAP)—(PG)—(T)—(PG)—(T)—(PG)—(CAP).

EXAMPLE II

An ester composition made from m-sulfobenzoic acid monosodium salt, 1,2-propylene glycol, and dimethyl terephthalate. The example illustrates an ester composition according to the invention which is less preferred than that of Example I since ester is present which is singly end-capped or is not end-capped.

The synthesis of Example I is repeated, with the following two changes:

(a) only 40.0 g of m-sulfobenzoic acid monosodium salt is used; and (b) in the final step of the reaction, during which the mixture is heated and stirred in the Kugelrohr apparatus at 200° C., a time of only 1 hour is used.

The product has the empirical formula representation:

$(CAP)_1(PG)_4(T)_3$

As in Example I, the composition is novel in that a significant proportion of doubly end-capped oligomers is present. Also present are novel singly-capped ester molecules, as illustrated by:

(CAP)—(PG)—(T)—(PG)—(T)—(PG)—(T)—(PG)—H.

The composition also contains known materials, such as unreacted 1,2-propylene glycol and some uncapped ester, as illustrated by:

H—(PG)—(T)—(PG)—H and
H—(PG)—(T)—(PG)—(T)—(PG)—H.

EXAMPLE III

An ester composition made from m-sulfobenzoic acid monosodium salt, 1,2-propylene glycol, ethylene glycol and dimethyl terephthalate. The example illustrates an ester composition according to the invention wherein the doubly-capped ester molecules have a "hybrid" backbone, i.e., they contain a mixture of essential and nonessential oxy-1,2-alkyleneoxy units.

Into a 1000 ml, three-necked, round bottom flask, fitted with a thermometer, magnetic stirrer and modified Claisen head, the latter connected to a condenser and receiver flask, are placed, under argon, m-sulfobenzoic acid monosodium salt (89.6 g; 0.40 moles; Eastman Kodak), 1,2-propylene glycol (144.6 g; 1.90 moles; Aldrich), ethylene glycol (236.0 g; 3.80 moles; Mallinckrodt), and hydrated monobutyltin(IV) oxide (0.6 g; 0.1% w/w; sold as FASCAT 4100 by M&T Chemicals). Over a five hour period, the mixture is stirred and heated under argon at atmospheric pressure, to reach a temperature of 175° C. The reaction conditions are kept constant for an additional 16 hours, during which time distillate (12.2 g; 164% based on the theoretical yield of water) is collected. The reaction mixture is cooled to about 100° C., and dimethyl terephthalate (145.5 g; 0.75 moles; Union Carbide) is added under argon. Over a 4 hour period, the mixture is stirred and heated under argon at atmospheric pressure, to reach a temperature of 175° C. The reaction conditions are kept approximately constant (temperature range 175°-180° C.) for a further 18 hours, during which time distillate (48.9 g; 102% of theory based on the calculated yield of methanol) is collected. The mixture is cooled to about 50° C. and is transferred under argon to a Kugelrohr apparatus (Aldrich). The apparatus is evacuated to a pressure of 1 mm Hg. While maintaining the vacuum and stirring, the temperature is raised to 200° C. over 20 hours. Reaction conditions are then held constant for about 4.5 hours to allow completion of the synthesis. During this period, excess glycol distills from the homogeneous mixture.

Using the convention introduced above, the product of Example III has the empirical formula representation:

$(CAP)_2(EG/PG)_{4.75}(T)_{3.75}$.

In this representation, (CAP) represents the m-sulfobenzoyl end-capping units, in sodium salt form. The mole ratio of oxyethyleneoxy and oxy-1,2-propyleneoxy units is determined spectroscopically to be about 4:1; the volatility and reactivity differentials of the parent glycols are responsible for the difference between this observed ratio and the ratio predicted on the basis of moles of the two glycols used.

Illustrative of structures of oligomeric ester molecules present in the composition of Example III is:

(CAP)—(EG)—(T)—(PG)—(T)—(EG)—(T)—(PG)—(CAP).

EXAMPLES IV-IX

Ester compositions made from simple reactants capable of providing sulfobenzyl end-capping units having different isomeric forms and chemical compositions, using 1,2-propylene glycol and dimethyl terephthalate as co-reactants. The examples also include illustration of the use of cations other than sodium associated with the sulfonate anion, and simulate incompletely sulfonated end-capping reactant.

The procedure of Example I is in each instance reproduced, with the single exception that the m-sulfobenzoic acid monosodium salt (50.0 g; 0.22 moles) used in Example I is replaced with an equimolar amount of the following:

Example IV o-sulfobenzoic acid monopotassium salt (prepared from the anhydride)

Example V

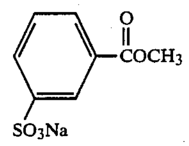

Example VI: o-sulfobenzoic acid monosodium salt (prepared from the anhydride, Eastman Kodak)

Example VII: a mixture, having the following composition (weight %): m-sulfobenzoic acid monosodium salt, 92%; p-sulfobenzoic acid monopotassium salt (Eastman Kodak), 6%; o-sulfobenzoic acid monosodium salt, 2%.

Example VIII: a mixture having the following composition (weight %): m-sulfobenzoic acid monosodium salt, 50%; o-sulfobenzoic acid monosodium salt, 50%.

Example IX: a mixture having the following composition (weight %): m-sulfobenzoic acid monosodium salt, 92%; para-sulfobenzoic acid monopotassium salt (Eastman Kodak), 6%; o-sulfobenzoic acid monosodium salt, 1%; benzoic acid (Aldrich), 1%.

EXAMPLE X

An ester composition is made from m-sulfobenzoic acid monosodium salt, 5-sulfoisophthalic acid monosodium salt, 1,2-propylene glycol, ethylene glycol and dimethyl terephthalate. The example illustrates an ester composition according to the invention wherein the doubly-capped ester molecules not only have sulfonated end-capping units, but also incorporate sulfonated units in the ester backbone.

Into a 500 ml, three-necked, round bottom flask, fitted with a thermometer, magnetic stirrer and modified Claisen head, the latter connected to a condenser and receiver flask, are placed, under argon, m-sulfobenzoic acid monosodium salt (22.4 9; 0.10 moles; Eastman Kodak), 5-sulfoisophthalic acid, mono- sodium salt (26.8 g; 0.10 moles; Aldrich), 1,2-propylene glycol (137.4 g; 1.8 moles; Mallinckrodt), ethylene glycol (149.3 g; 2.4 moles; Fisher), and hydrated monobutyltin(IV) oxide (0.4 g; 0.1% w/w; sold as FASCAT 4100 by M&T Chemicals). Over a 6 hour period, the mixture is stirred and heated under argon at atmospheric pressure, to reach a temperature of 175° C. The reaction conditions are kept constant for an additional 17 hours, during which time distillate (8.2 g; 152% based on the theoretical yield of water) is collected. The reaction mixture is cooled to about 100° C., and dimethyl terephthalate (106.2 g; 0.55 moles; Aldrich) is added under argon. Over a 3 hour period, the mixture is stirred and heated under argon at atmospheric pressure, to reach a temperature of 175° C. The reaction conditions are kept approximately constant (temperature range 175°-180° C.) for a further 18 hours, during which time distillate (36.9 g; 105% of theory based on the calculated yield of methanol) is collected. The mixture is cooled to about 50° C. and is transferred under argon to a Kugelrohr apparatus (Aldrich). The apparatus is evacuated to a pressure of 1 mm Hg. While maintaining the vacuum and stirring (reciprocating stirrer action) the temperature is raised to 200° C. This temperature is maintained for 5 hours, and is then increased and held at 220° C. for 3 hours to complete the synthesis; during this period, excess glycols distill from the homogeneous mixture.

Using the convention introduced above, the product of Example X has the empirical formula representation $(CAP)_2(EG/PG)_{14}(T)_{11}(SIP)_2$ Illustrative of structures of individual ester molecules in the Example X composition are:

(CAP)—(PG)—(T)—(PG)—(T)—(EG)—(T)—(PG)—(SIP)—(PG)—H (minor component)

and (CAP)—(PG)—(T)—(PG)—(T)—(PG)—(T)—(EG)—(SIP)—(PG)—(T)—(EG)—(T)—(PG)—(SIP)—(EG)—(CAP)

(illustrative of major component).

EXAMPLE XI

An ester composition is made from m-sulfobenzoic acid monosodium salt, polyethylene glycol (PEG-3400), 1,2-propylene glycol and dimethyl terephthalate. The example illustrates an ester composition according to the invention wherein the doubly-capped ester molecules not only have sulfonated end-capping units by way of hydrophilic units, but also incorporate uncharged, i.e., nonionic, hydrophilic units in the ester backbone. Also illustrated is a catalyst addition sequence differing from that of the previous examples.

Into a 250 ml, three-necked, round bottom flask, fitted with a thermometer, magnetic stirrer and modified Claisen head, the latter connected to a condenser and receiver flask, are placed, under argon, m-sulfobenzoic acid monosodium salt (13.2 g; 0.059 moles; Eastman Kodak) and 1,2-propylene glycol (35.7g, 0.47 moles, Fisher). The mixture is stirred and heated steadily under argon at atmospheric pressure, to reach a temperature of about 200° C. The reaction conditions are kept constant, while distillate (1.06 g; 100% based on the theoretical yield of water) is collecting in the receiver flask, and the temperature is then allowed to fall to about 170°-175° C. To the clear, colorless reaction mixture are added, under argon, hydrated monobutyltin(IV) oxide (0.2 g; 0.1% w/w; sold as FASCAT 4100 by M&T Chemicals), dimethyl terephthalate (45.0 g; 0.23 moles; Aldrich), and (100.0 g; 0.029 moles; n averages 77; m.w. =3400; Aldrich). Also added, as antioxidant, is BHT (0.2 g, Aldrich). Over 18–19 hours, the mixture is stirred and heated under argon at atmospheric pressure, at temperatures ranging from about 175°–195° C.; this reaction period is followed by a further 4 hour reaction period in which all reaction conditions, with the exception of temperature (now raised to about 200° C.), are unchanged. The methanol which is liberated in the transesterification is continuously collected. The mixture is cooled to about 50° C. and is transferred under argon to a Kugelrohr apparatus (Aldrich). The apparatus is evacuated to a pressure of 0.1 mm Hg. While maintaining the vacuum and stirring (reciprocating action), the temperature is raised to 200° C., and the temperature is then held constant for about 10 hours to allow completion of the synthesis. (In an alternative procedure n.m.r. spectroscopic monitoring confirms that the reaction is substantially complete after only 6–8 hours.) During this period, excess glycols distill from the homogeneous mixture.

Using the convention introduced above, the product of Example XI has the empirical formula representation:

$(CAP)_2(PG\ E_{77})_1$

Illustrative of the novel doubly end-capped ester molecules of this composition are:

(CAP)—(PG)—(T)—($E_{77}$)—(T)—(PG)—(T)—(PG)—(T)—(PG)—(T)—(PG)—(CAP)

and (CAP)—(PG)—(T)—(PG)—(T)—(PG)—(T)—(PG)—(T)—($E_{77}$)—(T)—(PG)—(T)—(PG)—(T)—(PG)—(T)—(PG)—(CAP)

EXAMPLE XII

An ester composition is made from m-sulfobenzoic acid monosodium salt, polyethylene glycol (PEG-3400), 1,2-propylene glycol and dimethyl terephthalate. The example illustrates an ester composition according to the invention which is prepared by a procedure identical with that of Example XI, with the two exceptions that (a) inert gas sparging is used in replacement of the procedure carried out in the Kugelrohr apparatus as described hereinabove; and (b) all reactant quantities are scaled up by a factor of 10, with glassware sizes being correspondingly increased.

The example illustrates that this procedural variation is acceptable for preparing ester compositions according to the invention, thereby allowing scale-up from the rather small Kugelrohr apparatus.

The scaled-up procedure of Example XI is carried out to the stage at which the reaction mixture would normally be transferred to the Kugelrohr apparatus. A PYREX gas dispersion tube, having attached at one end an argon supply, and at the opposite end a coarse (40–60 micron) glass frit, is inserted into a side-arm of the apparatus so that it reaches well below the surface of the liquid reaction mixture. With a rapid flow of argon through the mixture, venting to the exterior of the apparatus so as to allow entrainment of glycols, the mixture is heated to about 200° C. and stirred, for about 48 hours. At this time, the mixture is cooled and sampled The product is spectroscopically identical with that of Example XI.

EXAMPLE XIII

An ester composition is made from m-sulfobenzoic acid monosodium salt, 1,2-propylene glycol and dimethyl terephthalate. The example illustrates an ester composition according to the invention which is prepared by a procedure identical with that of Example I, with the single exception that a different catalyst is used.

The procedure of Example I is repeated, with the single exception that $Sb_2O_3$ (0.6g; 0.002 moles; Fisher) and calcium acetate monohydrate (0.6g; 0.003 moles, MCB) are used as replacement for the tin catalyst of Example I. The product of this example has a slightly darker color, but is otherwise similar to that prepared by the unchanged Example I procedure.

EXAMPLES XIV–XV

Ester compositions are made from m-sulfobenzoic acid monosodium salt, dimethyl terephthalate, and cyclic carbonates. The examples illustrate one ester composition according to the invention in which the essential oxy-1,2-alkyleneoxy units are provided in the form of oxy-1,2-butyleneoxy units, and another which is prepared by use of an alternative source of oxy-1,2-propyleneoxy units.

Sources of starting materials for these examples are as reported in the preceding examples, except that the cyclic carbonates are preparable using the above-incorporated procedure of Fagerburg. One source of the 1,2-diol reagent $EtCH(OH)CH_2OH$, needed for the provision of cyclic carbonate and likewise useful herein without carbonate derivatization, is provided by Kato (CA 51:11202 g), which is likewise incorporated herein by reference. (The lower 1,2 alkane diols can also be purchased from the Aldrich Chemical Co.)

The same procedure is used for both Example XIV and Example XV, and is as follows:

Into a 250 ml, three-necked, round bottom flask, fitted with a thermometer, magnetic stirrer and modified Claisen head, the latter connected to a condenser and receiver flask, are placed, under argon, 4-ethyl-1,3-dioxolan-2-one (52g; 0.45 moles), terephthalic acid (31.6 g; 0.19 moles; Aldrich), and m-sulfobenzoic acid monosodium salt (22.4 g; 0.1 moles; Eastman Kodak). Hydrated monobutyltin (IV) oxide (0.2 g; 0.2% w/w; M&T Chemicals) is added. The mixture is stirred and heated steadily under argon at atmospheric pressure, to melt and reach a temperature of about 200° C. The reaction conditions are kept constant, for about 24 hours while a small volume of aqueous distillate collects in the receiver flask. At this point, the mixture is clear and homogeneous, and distillate collection appears to have ceased. The mixture is cooled to about 100° C. and is transferred under argon to a Kugelrohr apparatus (Aldrich). The apparatus is evacuated to a pressure of about 0.1 mm Hg. While maintaining the vacuum and reciprocating stirring, the temperature is raised to 200° C., and the temperature is then held constant for about 10 hours to allow completion of the synthesis. During this period, excess glycols distill from the homogeneous mixture.

The composition of the Example XIV product is expressed by the empirical formula:

$(CAP)_2(2G)_{4.75}(T)_{3.75}$ wherein (2G) represents unsymmetrical oxy-1,2-alkyleneoxy units, which have structure differing from oxy-1,2-propyleneoxy units only in that the former have ethyl side-chains, in contrast with the methyl side-chains of the latter.

Repetition of the above procedure, using 1,2-propylene carbonate in replacement of the ethyl-substituted cyclic carbonate, leads to formation (Example XV) of an ester composition represented by:

$(CAP)_2(PG)_{4.75}(T)_{3.75}$

Structures of illustrative ester molecules of the compositions of Examples XIV and XV are, respectively, similar to and identical with structures depicted in Example I.

Use of Esters of the Invention as Soil-Release Agents

Esters of the invention are especially useful as soil release agents of a type compatible in the laundry with conventional detersive and fabric-conditioner ingredients (such as those found in granular detergents and dryer-added sheets, respectively). The ester compositions, as provided herein, will typically constitute from about 0.1% to about 10% by weight of a granular detergent and from about 1% to about 70% by weight of a dryer-added sheet. See the following patents, all incorporated herein by reference, for detailed illustrations of granular detergent compositions and articles, such as dryer-added sheets, suitable for use in combination with the soil release esters herein; these patents include disclosures of types and levels of typical detersive surfactants and builders, as well as of fabric conditioner active ingredients useful herein: U.S. Pat. Nos. 3,985,669, Krummel et al., issued Oct. 12, 1976; 4,379,080, Murphy, issued Apr. 5, 1983; 4,490,271, Spadini et al., issued Dec. 25, 1984 and 4,605,509, Corkill et al., issued Aug. 12, 1986 (in the foregoing, granular detergent compositions have non-phosphorus builder systems; other non-phosphorus builders usable herein are the compounds tartrate monosuccinate/tartrate disuccinate, disclosed in U.S. Pat. No. 4,663,071, Bush et al., issued May 5, 1987 and 2,2 -oxodisuccinate, disclosed in U.S. Pat. No. 3,128,287, Berg, issued Apr. 7, 1964). Phosphorus-containing builders well-known in the art can also be used, as can bleaches; see U.S. Pat. No. 4,412,934, Chung et al., issued Nov. 1, 1983. Articles for use in automatic tumble-dryers are illustrated in more detail in U.S. Pat. Nos. 3,442,692, Gaiser, issued May 6, 1969; 4,103,047, Zaki et al., issued July 25, 1978 and 3,686,025, Morton, issued Aug. 22, 1972.

Ester compositions of the invention, at aqueous concentrations ranging from about 1 to about 50 ppm, more preferably about 5 to about 30 ppm, provide effective, combined cleaning and soil release treatments for polyester fabrics washed in an aqueous, preferably alkaline (pH range about 7 to about 11, more preferably about 9 to about 10.5) environment, in the presence of typical granular detergent ingredients; including anionic surfactants, phosphate, ether carboxylate or zeolite builders, and various commonly used ingredients such as bleaches, enzymes and optical brighteners. Surprisingly (especially insofar as pH and anionic surfactant are concerned), all of these detergent ingredients can be present in the wash water at their art disclosed levels, to perform their conventional tasks, e.g., for cleaning and bleaching fabrics or the like, without ill-effects on the soil release properties of the esters.

Thus the invention encompasses a method of laundering fabrics and concurrently providing a soil release finish thereto. The method simply comprises contacting said fabrics with an aqueous laundry liquor containing the conventional detersive ingredients described hereinabove, as well as the above-disclosed effective levels of a soil release agent (namely, from about 1 to 50ppm of an oligomeric or polymeric composition comprising at least 10% by weight of an ester of the invention). Although this method is not especially limited in terms of factors such as pH and surfactant types present, it should be appreciated that for best cleaning of fabrics, it is often especially desirable to make use, in the laundry process, of anionic surfactants, such as conventional linear alkylbenzene sulfonates, and also to use higher pH ranges as defined above. Use of these surfactants and pH ranges surprisingly does not prevent the esters of the invention from acting effectively as soil release agents. Thus, a preferred method, for an optimized combination of cleaning and soil-release finishing, provided by the invention, constitutes using all of the following:

the preferred levels of soil release agent (5–30ppm);

anionic surfactant;

pH of from about 7 to about 11; and, by way of soil release agent, a preferred composition of the invention, such as the oligomeric product of reacting compounds comprising sulfobenzoic acid or a $C_1$–$C_4$ alkyl carboxylate ester thereof as the monosodium salt, dimethyl terephthalate and 1,2-propylene glycol (see, for example the methods for making and examples, such as Example I, hereinabove for further details).

In the preferred method, polyester fabrics are used; best soil release results are achieved thereon, but other fabric types can also be present.

The most highly preferred method for simultaneous cleaning and soil-release treatment is a "multi-cycle" method; although benefits are surprisingly obtainable after as little treatment as a single laundry/use cycle, best results are obtained using two or more cycles comprising the ordered sequence of steps:

(a) contacting said fabrics with said aqueous laundry liquor in a conventional automatic washing machine for periods ranging from about 5 minutes to about 1 hour;

(b) rinsing said fabrics with water;

(c) line- or tumble-drying said fabrics; and (d) exposing said fabrics to soiling through normal wear or domestic use.

Naturally, it will be appreciated that this "multi-cycle" method encompasses methods starting at any one of steps (a) through (d), provided that the soil release treatment step (a) is used two or more times.

In the above, hand-washing provides an effective but less preferred variant in step (a), wherein U.S. or European washing machines operating under their conventional conditions of time, temperature, fabric load, amounts of water and laundry product concentrations will give the best results. Also, in step (c), the "tumble-drying" to which is referred especially involves use of conventional domestic brands of programmable laundry dryers (these are occasionally integral with the washing machine), also using their conventional fabric loads, temperatures and operating times.

The following nonlimiting examples illustrate the use of a typical ester composition of the invention (that of Example III) as a soil release agent for thru-the-wash application to polyester fabrics.

EXAMPLES XVI-XVIII

Granular detergent compositions comprise the following ingredients:

| | Percent (Wt) | | |
|---|---|---|---|
| Ingredient | XVI | XVII | XVIII |
| $C_{11}$–$C_{13}$ alkyl benzene sulfonate | 7.5 | 4.0 | 12.0 |
| $C_{12}$–$C_{13}$ alcohol ethoxylate (EO 6.5) | 1.0 | 0.0 | 1.0 |
| Tallow alcohol sulfate | 7.5 | 6.5 | 7.5 |
| Sodium tripolyphosphate | 25.0 | 39.0 | 0.0 |
| Sodium pyrophosphate | 6.0 | 0.0 | 0.0 |
| Zeolite A, hydrate (1-10 micron size) | 0.0 | 0.0 | 29.0 |
| Sodium carbonate | 17.0 | 12.0 | 17.0 |
| Sodium silicate (1:6 ratio $NaO/SiO_2$) | 5.0 | 6.0 | 2.0 |
| Balance (can, for example, include water, soil dispersant, bleach, optical brightener, perfume, suds suppressor or the like) | | to 98.0 | |

Aqueous crutcher mixes of the detergent compositions are prepared and spray-dried, so that they contain the ingredients tabulated, at the levels shown. The ester composition of Example I is pulverized in an amount sufficient for use at a level of 2% by weight in conjunction with the detergent compositions.

The detergent granules and ester composition are added (98 parts/2 parts by weight, respectively), together with a 6 lb. load of previously laundered and soiled fabrics (load composition: 20 wt. % polyester fabrics/80 wt. % cotton fabrics), to a Sears KENMORE washing machine. Actual weights of detergent and ester compositions are taken to provide a 1280 ppm concentration of the former and 30 ppm concentration of the latter in the 17 l water-fill machine. The water used has 7 grains/gallon hardness and a pH of 7 to 7.5 prior to (about 9 to about 10.5 after) addition of the detergent and ester compositions.

The fabrics are laundered at 35° C. (95° F.) for a full cycle (12 min.) and rinsed at 21° C. (70° F.). The fabrics are then line dried and are exposed to a variety of soils (by wear or controlled application). The entire cycle of laundering and soiling is repeated several times for each of the detergent compositions, with separate fabric bundles reserved for use with each of the detergent compositions. Excellent results are obtained in all cases (XVI-XVIII), especially in that polyester or polyester-containing fabrics laundered one or, more preferably, several times as described, display significantly improved removal of soils (especially oleophilic types) during laundering compared with fabrics which have not been exposed to the esters of the invention.

What is claimed is:

1. A method of laundering fabrics and concurrently providing a soil release finish thereto, comprising contacting said fabrics with an aqueous laundry liquor containing conventional detersive ingredients and from about 1 to about 50 ppm of a soil release agent which is an oligomeric or polymeric composition comprising at least 10% by weight of a substantially linear, sulfoaroyl end-capped ester having a molecular weight ranging from about 500 to about 20,000; wherein said ester consists essentially of, on a molar basis, (i) from about 1 to about 2 moles of sulfobenzoyl end-capping units of the formula $(MO_3S)$ $(C_6H_4)$ C(O)— wherein M is a salt-forming cation;

(ii) from about 2 to about 50 moles of oxy - 1, 2-propyleneoxy units of mixtures thereof with oxyethyleneoxy units provided that the oxy - 1, 2-propyleneoxy: oxyethyleneoxy mole ratio is in the range from about 1:10 to about 1.0; and (iii) from about 1 to about 40 moles of terephthaloyl units provided that the mole ratio of said units identified by (ii) and (iii) is from about 2:1 to about 1:24.

2. A method according to claim 1 wherein said conventional detersive ingredients comprise one or more conventional anionic surfactants; said soil release agent is present at a level of from about 5 to about 30 ppm in said aqueous laundry liquor and is further characterized in that it consists essentially of the oligomeric product of reacting compounds comprising sulfobenzoic acid or a $C_1$–$C_4$ alkyl carboxylate ester thereof as the monosodium salt, dimethyl terephthalate, and 1,2-propylene glycol; said fabrics consist essentially of polyester fabrics; and said aqueous laundry liquor is further characterized in that it has a pH from about 7 to about 11.

3. A method according to claim 2 wherein said fabrics are subjected to two or more cycles comprising the ordered sequence of steps:

(a) contacting said fabrics with said aqueous laundry liquor in a conventional automatic washing-machine for periods ranging from about 5 minutes to about 1 hour;

(b) rinsing said fabrics with water;

(c) line- or tumble-drying said fabrics; and (d) exposing said fabrics to soiling through normal wear or domestic use.

* * * * *

UNITED STATES PATENT AND TRADEMARK OFFICE

CERTIFICATE OF CORRECTION

PATENT NO. : 4,976,879

DATED : December 11, 1990

INVENTOR(S) : Rene Maldonado et al

It is certified that error appears in the above-identified patent and that said Letters Patent is hereby corrected as shown below:

Column 5, line 21, "of o the estes" should read --of the esters--.

Column 5, line 29, "sulfonated carbonyl" should read --sulfonated dicarbonyl--.

Column 5, line 43, "about to about 2" should read --about 1 to about 2--.

Column 9, line 25, "Molecular Units The" should read --Molecular Units - The--.

Column 9, line 58, "$-OCH_2CH(CH_3)CH_2O-$" should read -- $-OCH(CH_3)CH_2O-$ --.

Column 13, lines 44-45, "unkown" should read --unknown--.

Column 22, line 61, "(provided" should read --provided --.

Column 26, line 67, "and (100.0 g;" should read --$HO(CH_2CH_2O)_nH$ (100.0g;--.

Column 27, line 24, "$(CAP)_2(PG\ E77)_1$," should read --$(CAP)_2(PG)_8(T)_8(E_{77})_1$,--.

Signed and Sealed this

Twelfth Day of January, 1993

*Attest:*

DOUGLAS B. COMER

*Attesting Officer*

*Acting Commissioner of Patents and Trademarks*